(12) United States Patent
Åström

(10) Patent No.: US 7,086,172 B2
(45) Date of Patent: Aug. 8, 2006

(54) GRID FOR GUIDED OPERATIONS

(75) Inventor: Gunnar Åström, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 0 days.

(21) Appl. No.: 10/777,223

(22) Filed: Feb. 13, 2004

(65) Prior Publication Data
US 2005/0004581 A1    Jan. 6, 2005

(30) Foreign Application Priority Data
Jul. 3, 2003    (SE) .................................... 0301977

(51) Int. Cl.
*G01B 3/14*    (2006.01)
*H05G 1/28*    (2006.01)

(52) U.S. Cl. .......................... 33/563; 378/164
(58) Field of Classification Search .......... 33/562–566, 33/512, 435, 492, 494, 1 B, 1 BB, 485; 378/162–165; 606/130; 600/407
See application file for complete search history.

(56) References Cited

U.S. PATENT DOCUMENTS

| | | | | | |
|---|---|---|---|---|---|
| 2,245,469 | A | * | 6/1941 | Ecklund et al. | 7/163 |
| D142,608 | S | * | 10/1945 | Ziegfeld | D10/62 |
| 3,547,121 | A | * | 12/1970 | Cherry | 604/116 |
| 4,171,573 | A | * | 10/1979 | Picciotto | 33/1 B |
| 4,455,749 | A | * | 6/1984 | Hayward | 33/1 B |
| 4,838,265 | A | * | 6/1989 | Cosman et al. | 606/1 |
| 4,860,331 | A | * | 8/1989 | Williams et al. | 378/163 |
| 4,918,715 | A | * | 4/1990 | Krupnick et al. | 378/164 |
| 5,216,700 | A | * | 6/1993 | Cherian | 378/163 |
| 5,260,985 | A | | 11/1993 | Mosby | |
| 5,285,785 | A | * | 2/1994 | Meyer | 600/426 |
| 5,427,099 | A | * | 6/1995 | Adams | 600/414 |
| 5,444,920 | A | * | 8/1995 | Nelson | 33/494 |
| 5,961,455 | A | * | 10/1999 | Daum et al. | 600/407 |
| 6,333,970 | B1 | * | 12/2001 | LeMaitre et al. | 378/162 |
| 6,714,628 | B1 | * | 3/2004 | Broyles et al. | 378/164 |
| D507,053 | S | * | 7/2005 | Åkerfeldt et al. | D24/158 |

FOREIGN PATENT DOCUMENTS

DE    100 27 275 A1    1/2002
WO    WO 02/059571 A2    8/2002

OTHER PUBLICATIONS

Information—Packing, printed Feb. 12, 2004, 8 pages.
CT Guide—A guidance device use in CT-guided biopsies, Radi Medical Systems, 1990, 4 pages.

\* cited by examiner

*Primary Examiner*—G. Bradley Bennett
(74) *Attorney, Agent, or Firm*—Foley & Lardner LLP

(57) ABSTRACT

The invention relates to a grid (10) adapted to be arranged on a patient's skin to provide positioning information in CT-guided percutaneous operations. In one embodiment, the grid (10) comprises a flat and generally rectangular frame having two long sides (11*a*, 11*b*) and two short sides (12*a*, 12*b*), with a number of transverse ribs (13, 14) being provided between the two long sides (11*a*, 11*b*). According to the invention, at least some of the transverse ribs (13, 14) are elastic. By using his/her fingers, a doctor can thereby separate two neighbouring ribs (13, 14) such that an opening is provided in the grid (10). Through this opening access is obtained to the skin area under the grid (10), or the grid (10) can be threaded over and removed from a medical instrument which, between two adjacent ribs (13, 14), is inserted into the patient's body.

12 Claims, 1 Drawing Sheet

GRID FOR GUIDED OPERATIONS

FIELD OF THE INVENTION

The present invention relates generally to a medical guidance device for use in guided medical operations (for example, CT-guided operations), and in particular to a grid with which the correct entrance position for a biopsy instrument can be determined during a CT-guided biopsy operation.

BACKGROUND OF THE INVENTION

In a medical operation involving the percutaneous insertion of an elongated instrument to a predetermined position within a patient's body, the direction and the insertion depth as well as the entrance position at the patient's skin have to be determined. When the medical operation in question is a biopsy operation performed by means of computerized tomography (CT), the direction and the insertion depth can be calculated from coordinates given on a CT screen. Regarding the entrance position, a CT scanner provides information about where a particular picture of a slice has been taken, i.e. the position along the length of a patient's body is known, but the position transverse to the body extension is unknown. Both a transverse coordinate and a longitudinal coordinate are needed to determine a correct entry point. To facilitate the establishment of the correct entry point at the skin surface, some kind of grid can be arranged on the skin at the approximated entry area.

In its simplest form, such a grid may consist of a number of catheters or similar items that the medical personnel attach on the skin surface. A more dedicated grid has, however, previously been proposed by the assignee of the present applicant. This grid consisted essentially of a generally rectangular frame, with a number of transverse grid bars extending between the long sides of the rectangular frame. The grid was intended and designed for use together with a special CT-guidance device, and its construction regarding versatility and user-friendliness can be improved.

SUMMARY OF THE INVENTION

As mentioned above, the previously known grid was designed to be used in combination with a special CT-guided biopsy device. The construction of this CT guide did not allow for the removal of the grid over an instrument, such as a biopsy needle, introduced in a patient's body. Consequently, the grid was not designed to be removable and repositionable. It has now, however, been realized that it is advantageous to be able to remove and reposition a grid during a biopsy operation. It has further been recognized that during, for example, a biopsy operation, there can be a need for extra palpation of the area under which the tissue of interest is disposed.

One object of the present invention is to provide an improved grid comprising a flat frame provided with transverse ribs or bars, the improvement being that the transverse ribs are elastic such that two adjacent ribs can be stretched and separated from each other. An opening is thereby created, by which the grid can be threaded over a biopsy instrument introduced between the two ribs. With a grid having elastic ribs, it is also possible to palpate the area below the grid without removing the grid, something that can be of considerable advantage when the grid is attached to a patient's skin by, for example, adhesive tape or adhesive provided at the underside of the grid.

Furthermore, when determining between which two grid ribs a percutaneous operation is to be performed, a doctor must decide if the respective ordinal number of a rib is counted from the left or right side of the grid. A grid should therefore preferably be equipped with some kind of markings that enable a doctor to unambiguously distinguish the right side of the grid from the left side. A distinguishing feature of this kind is even more valuable when the grid is a removable and repositionable grid—as provided by the present invention—because the risk of accidentally rotating the grid 180° during repositioning of the grid should be eliminated. In one embodiment of the present invention, one of the sides of the grid frame is therefore provided with an enlarged width in comparison with the opposite side, whereby the risk of accidentally rotating the grid 180° is avoided.

DETAILED DESCRIPTION OF A PREFERRED EMBODIMENT

Figure 1:
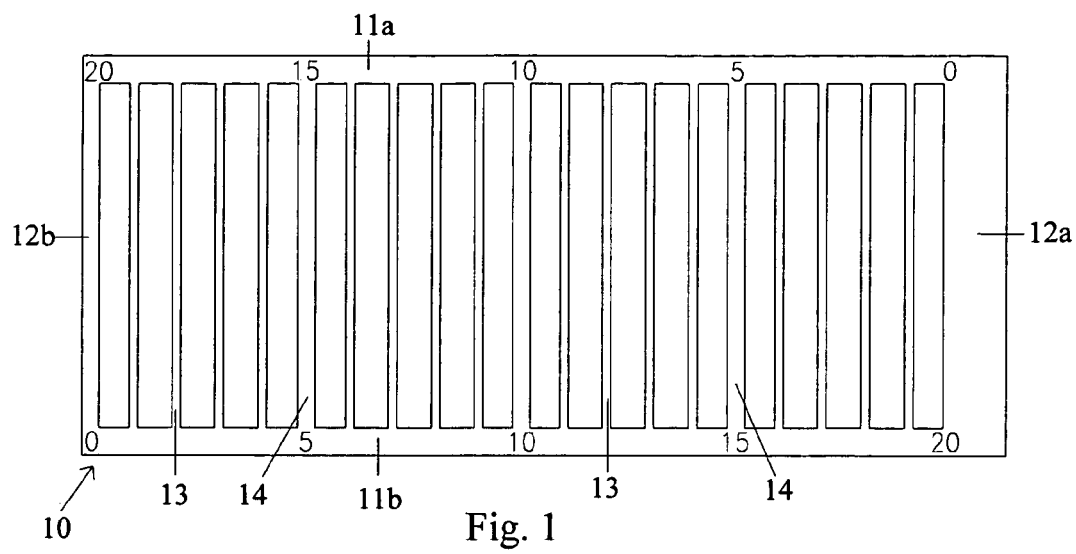
FIG. 1 shows a grid according to the present invention in an unstretched state.

In FIG. 1, a grid 10 according to the present invention is illustrated. The grid 10 comprises a generally flat and rectangular frame having two long sides 11a, 11b and two short sides 12a, 12b. Several transverse bars or ribs 13, 14 are connected to the long sides 11a, 11b. To strengthen the frame and to facilitate the determination of between which of the ribs a puncture is to be performed, some of the ribs have been given a larger width than the other ribs. As can be seen from FIG. 1, each fifth rib is broader than the intermediate ribs. These broader ribs have been marked with reference numeral 14, and the frame is also provided with numbers (in this example, 0, 5, 10 and 20) that represent the ordinal number of the respective rib. It should further be noted that one of the short sides (short side 12a in FIG. 1) has been given a larger width than the opposite short side 12b. The purpose and advantage of the latter feature will become apparent from the description below.

In one embodiment of the invention using a grid fabricated from a thermoplastic elastomer, which is sold by Polykemi AB under the trademark POLYelast (as described in www.polykemi.se/pdflib/POLYELAST.pdf, whose entire contents are incorporated herein by reference), with barium in the form of barium sulfate added, the elasticity of the ribs is designed such that a rib can be moved (by using finger tips) into contact with an adjacent rib, and when the rib is released it resumes its original position within a few seconds and without being damaged by inelastic strain. Thus, in this embodiment, the distance between two neighboring ribs can readily be tripled. Advantages of this feature will be discussed below. In this embodiment, the overall flexibility of the grid (ribs plus frame) is such that when the grid is placed on a cylinder having a diameter of 130 mm, with the longest sides of the grid parallel to the circumference of the cylinder, 10 (plus or minus 2) ribs are in contact with the cylinder, without applying any external force to the grid.

Materials that provide the same or similar elasticity and flexibility may be used instead of this material. The grid preferably is made from a radiopaque material, so that the grid ribs appear clearly on a CT-scanned slice. Suitable materials for a CT application include polymers and copolymers (and/or mixtures thereof) which do not deform or degrade during sterilization and which include a radiopaque material such as barium. If the operation instead is performed by means of magnetic resonance (MR) tomography or positron emission tomography (PET), other suitable materials may be used. For MR application, the grid should act as a signal generator and may be formed with cavities containing a fluid with a contrast medium or may be formed with a contrast medium bound to the grid. The properties of the contrast medium can be set by an additive, such as gadolinium. For PET applications, materials with a large cross-section (high probability) for positron capture at energies at which positrons are emitted by isotopes (for example, oxygen-15, carbon-11, nitrogen-13, fluorine-18) which have been introduced into a patient's body. Materials other than those described above may be used.

The grid can be manufactured by injection molding, cutting or punching grids from a sheet or board, spraying or painting a grid on a surface and then peeling away the grid, or any other suitable technique.

Figure 2:
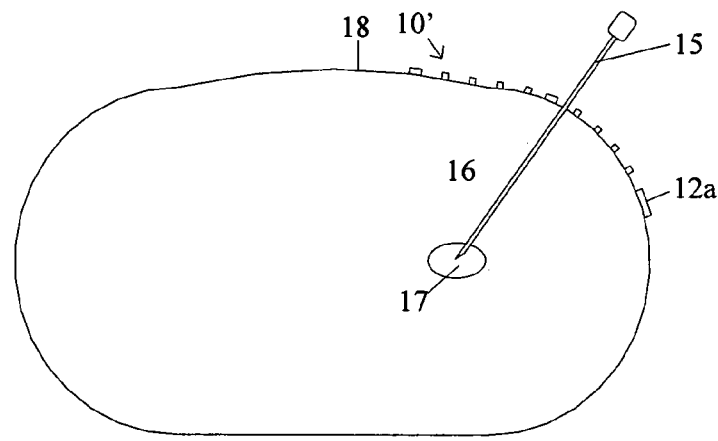
FIG. 2 is a schematic illustration of how a grid according to the invention is used in a biopsy operation.

FIG. 2 is a schematic illustration of a picture of a slice that can be obtained by a CT scanner during a medical operation in which a grid 10' (similar to that described above in connection with FIG. 1, but with less ribs) is used. The grid 10' of FIG. 1 has been arranged on a patient's skin 18. From the CT scanned slice it has been determined that the puncture should be performed between the fourth and fifth ribs of the grid 10', when counted from the short side 12a having the larger width. As can be seen from FIG. 2, a biopsy needle 15 has been introduced in the patient's body tissue 16, such that the distal end of the biopsy needle 15 is positioned within target tissue 17, while the proximal end of the biopsy needle 15 extends out of the patient's skin 18.

Instead of having a side with a larger width than the opposite side, one of the sides could be provided with another type of distinguishing feature, e.g. a recess or other formation, or one side could be made from a material that on a CT screen appears differently from the material in the opposite side.

Figure 3:
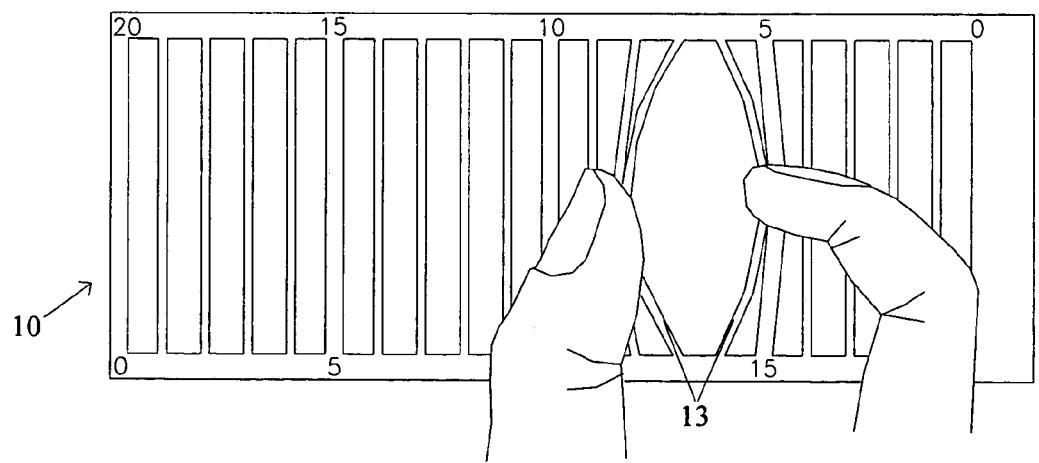
FIG. 3 shows the grid of FIG. 1 in a stretched state.

As mentioned above, it has now been realized that it can be desirable to remove a grid, with a medical instrument such as a biopsy needle still in place. For this purpose, the ribs of a grid according to the invention are designed to be elastic (as described above), such that the grid can be threaded over the biopsy needle. FIG. 3 illustrates how an opening is created in the grid 10 of FIG. 1. As illustrated in FIG. 3, by using his or her fingers a doctor or other medical personnel can separate two neighbouring ribs 13 such that an opening is provided. Without touching a biopsy instrument inserted between two ribs and thereby affecting its position, a doctor can therefore thread the grid 10 over a biopsy instrument that remains inserted into a patient's body. The underside of a grid according to the invention may be provided with an adhesive which allows the grid to be fixated to a patient's skin. To still have a removable grid, such an adhesive should be a releasable adhesive. Furthermore, the adhesive should preferably only be provided at the frame of the grid such that the grid ribs can be separated from each other.

One particular reason for removing a grid during a biopsy operation can be that further palpation is required, such that a doctor needs access to the skin area around the biopsy instrument to palpate underlying structures, e.g. bones, ribs or vessels, in order to perform a biopsy operation close to or between bones, and minimizing the risk of hitting susceptible structures with a biopsy needle. In this respect, the grid according to the present invention provides a further advantage. As may be appreciated from FIG. 3, palpation on the skin area surrounding a biopsy instrument can, at least in some cases, actually be carried out without removing the grid. That is, by stretching and separating the ribs such that an opening is created in the grid, a doctor acquires free access to a skin area at which palpation, or some other type of medical procedure, can be performed.

Although the present invention has been described with reference to a specific embodiment, also shown in the appended drawings, it will be apparent for those skilled in the art that many variations and modifications can be done within the scope of the invention as described in the specification and defined with reference to the following claims. For example, although a rectangular shape of the grid frame is presently regarded as the preferred embodiment of the invention, other shapes are within the scope of the invention. The grid frame could be quadratic (which is consider as a special case of a rectangular grid), triangular, or rhombic, or the grid frame could have more than four sides, including a circular shape. The ribs need not have the shape of a straight line. Further, some of these ribs, e.g. the ribs having a larger width, could be made from a less elastic or even non-elastic material, as long as it is possible to separate adjacent ribs enough to create an opening in the grid.

What is claimed is:

1. A grid adapted to be arranged on a patient's skin to provide positioning information in a guided percutaneous operation, comprising:
a frame configured to lie on and substantially conform to a patient and within which several ribs are arranged, wherein at least two adjacent ribs are homogeneous and elastic such that the elastic ribs are stretchable and then resume their original shape when released, and wherein at least some of the elastic ribs comprise at least one of a radiopaque material, a material visible in a magnetic resonance tomograph, and a material visible in a positron emission tomograph.

2. A grid according to claim 1, wherein some of said several ribs are broader, with a regular number of narrower ribs arranged therebetween.

3. A grid according to claim 1, wherein the grid is rectangular with two long sides, between which said several ribs are connected, and two short sides, of which one short side is distinguishably different from the other short side.

4. A grid according to claim 3, wherein one short side is broader than the opposite short side.

5. A grid according to claim 1, wherein the grid is provided with markings that show the ordinal number of the respective rib.

6. A grid according to claim 1, wherein the grid is radiopaque.

7. A grid according to claim 1, wherein the grid is made from a material that is visible in a magnetic resonance tomograph.

8. A grid according to claim 1, wherein the grid is made from a material that is visible in a positron emission tomograph.

9. A grid according to claim 1, wherein the underside of the grid at least partly is provided with an adhesive.

10. A grid according to claim 9, wherein the underside of the frame is provided with an adhesive.

11. A grid according to claim 1, wherein said at least two adjacent ribs comprise a thermoplastic elastomer and barium.

12. A grid according to claim 1, wherein said at least two adjacent ribs comprise a mixture of copolymers and a radiopaque material.

* * * * *